United States Patent
Wihl et al.

(10) Patent No.: US 6,917,421 B1
(45) Date of Patent: Jul. 12, 2005

(54) SYSTEMS AND METHODS FOR MULTI-DIMENSIONAL INSPECTION AND/OR METROLOGY OF A SPECIMEN

(75) Inventors: Tim Wihl, Fremont, CA (US); Stephen Hiebert, Milpitas, CA (US); Richard Schmidley, San Jose, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 11 days.

(21) Appl. No.: 10/266,333

(22) Filed: Oct. 8, 2002

Related U.S. Application Data
(60) Provisional application No. 60/329,034, filed on Oct. 12, 2001.

(51) Int. Cl.[7] ............................................... G01N 21/00
(52) U.S. Cl. ..................... 356/237.5; 356/614; 356/624
(58) Field of Search .......................... 356/237.1–237.5, 356/601, 609, 614, 622, 624, 630–632; 250/201.3, 201.4; 359/368

(56) References Cited

U.S. PATENT DOCUMENTS

| | | | | |
|---|---|---|---|---|
| 3,912,922 A | * | 10/1975 | Lacotte et al. .............. | 250/204 |
| 4,585,349 A | * | 4/1986 | Gross et al. ................ | 356/624 |
| 4,844,617 A | * | 7/1989 | Kelderman et al. ......... | 356/624 |
| 4,965,441 A | * | 10/1990 | Picard ...................... | 250/201.3 |
| 5,048,960 A | * | 9/1991 | Hayashi et al. ............. | 356/319 |
| 5,165,063 A | * | 11/1992 | Strater et al. ............... | 356/4.01 |
| 5,448,359 A | | 9/1995 | Schick et al. | |
| 5,608,529 A | * | 3/1997 | Hori .......................... | 356/609 |
| 5,608,564 A | | 3/1997 | Schick | |
| 5,629,773 A | * | 5/1997 | Wakai et al. ................ | 356/601 |
| 5,717,518 A | | 2/1998 | Shafer et al. | |
| 5,785,651 A | * | 7/1998 | Kuhn et al. ................. | 600/310 |
| 5,880,846 A | * | 3/1999 | Hasman et al. ............. | 356/602 |
| 5,912,735 A | | 6/1999 | Xu | |
| 5,956,174 A | | 9/1999 | Shafer et al. | |
| 6,064,517 A | | 5/2000 | Chuang et al. | |
| 6,133,576 A | | 10/2000 | Shafer et al. | |
| 6,181,472 B1 | | 1/2001 | Liu | |
| 6,208,411 B1 | | 3/2001 | Vaez-Iravani | |
| 6,268,923 B1 | | 7/2001 | Michniewicz et al. | |
| 6,313,467 B1 | | 11/2001 | Shafer et al. | |
| 2002/0018118 A1 | | 2/2002 | Coulombe et al. | |
| 2002/0085271 A1 | | 7/2002 | Shafer et al. | |

FOREIGN PATENT DOCUMENTS

| | | |
|---|---|---|
| DE | 197 31 291 | 1/1998 |
| GB | 2 315 562 | 2/1998 |
| GB | 2 357 158 | 6/2001 |
| WO | 01/71279 | 9/2001 |

OTHER PUBLICATIONS

SISCAN™ Optical 3D–Inspection, © by Siemens Dematic AG, 2001, 2 pages.

* cited by examiner

*Primary Examiner*—Hoa Q. Pham
(74) *Attorney, Agent, or Firm*—Ann Marie Mewherter; Daffer McDaniel, LLP (57) ABSTRACT

Systems and methods for assessing a dimension of a feature on a specimen are provided. A system may include an illumination system configured to scan the specimen with light at multiple focal planes substantially simultaneously. The system may also include a collection system that may include multiple collectors. Approximately all light returned from one of the multiple focal planes may be collected by one of the multiple collectors. In addition, the system may include a processor configured to determine a relative intensity of the collected light. The processor may also be configured to assess a dimension of the feature on the specimen in a direction substantially perpendicular to an upper surface of the specimen using the relative intensity.

20 Claims, 4 Drawing Sheets

SYSTEMS AND METHODS FOR MULTI-DIMENSIONAL INSPECTION AND/OR METROLOGY OF A SPECIMEN

PRIORITY CLAIM

This application claims priority to U.S. Provisional Application No. 60/329,034 entitled "Systems and Methods for Three-Dimensional Inspection and/or Metrology of a Specimen," filed Oct. 12, 2001.

BACKGROUND OF THE INVENTION

1. Field of the Invention

The present invention generally relates to systems and methods for three-dimensional inspection and/or metrology of a specimen. Certain embodiments relate to systems and methods for inspecting a specimen such as a bumped wafer with laser scanning chromatic confocal microscopy.

2. Description of the Relevant Art

Fabricating semiconductor devices such as logic and memory devices may typically include processing a specimen such as a wafer using a number of semiconductor fabrication processes to form various features and multiple levels of the semiconductor devices. For example, lithography is a semiconductor fabrication process that typically involves transferring a pattern to a resist arranged on a wafer. Additional examples of semiconductor fabrication processes may include, but are not limited to, chemical-mechanical polishing, etch, deposition, ion implantation, and plating. Multiple semiconductor devices may be fabricated in an arrangement on a wafer and then separated into individual semiconductor devices.

Prior to being separated into individual semiconductor devices, an entire wafer of semiconductor devices may be prepared for packaging. Packaging may include coupling a chip carrier such as a substrate to a semiconductor device. A chip carrier may provide mechanical strength, heat transfer, and environmental protection to a semiconductor device. In addition, a chip carrier may include electrical wiring or other electrical structures such that electrical connection may be made between a semiconductor device and another structure such as a card-on-board ("COB") structure for a computer system. Preparing a wafer of semiconductor devices for packaging may include forming structures on a surface of the semiconductor devices that may be used to couple a semiconductor device to a chip carrier. For example, relatively small solder balls may be arranged in an area on a semiconductor device. Such relatively small solder balls may be commonly referred to as "bumps," and a wafer on which such solder balls are formed may be commonly referred to as a "bumped wafer." The solder balls may be configured to physically attach the semiconductor device to a chip carrier and to make electrical connection to a chip carrier. For example, a device may be placed on a substrate, and the solder balls may contact and melt onto an array of metal pads on the substrate. Such a packaging method may be commonly referred to as face-down bonding, flip-chip bonding, or controlled collapse chip connections ("C4").

Bumps that are incorrectly formed on a wafer may cause significant problems during further processing such as probing of the wafer and during use of the device. For example, incorrectly formed bumps may damage probes on a probe card thereby causing tester downtime and incurring tester repair costs. Incorrectly formed bumps may also bridge power and ground contacts thereby resulting in excessive current draw through a probe card. Therefore, bumped wafers may typically be inspected and measured prior to probing. In addition, incorrectly formed bumps may not be detected during probing and may increase the potential for failure of a packaged device. Furthermore, probing may damage bumps especially on a wafer having a relatively high number of bumps per unit area that may require high vertical forces during testing to seat probes for proper contact. In this manner, inspection and metrology of a bumped wafer may also be performed after wafer probing.

Currently available methods for three-dimensional inspection, which may be commonly referred to as "defect detection," and metrology of bumped wafers generally include first acquiring data in the x-y plane and then acquiring data in the z plane. Essentially, such systems may be described as being serial in data acquisition (i.e., two-dimensional ("2D") data acquisition followed by three-dimensional ("3D") data acquisition). For bumped wafers, 2D defects may include, for example, missing bumps, improperly located bumps, bridged bumps, large-diameter bumps, and small-diameter bumps. Examples of 3D defects may include, but are not limited to, bumps that may be too tall or too short or that may have protruding vertical spikes or recessed vertical pits. Because currently available methods are generally not capable of simultaneous 2D and 3D data acquisition, such methods may be significantly slower than either 2D or 3D data acquisition. In addition, 3D data acquisition may be significantly slower than 2D data acquisition thereby resulting in substantially reduced sampling for 3D in comparison to sampling for 2D. As used herein, the term "sampling" may generally refer to the number of points or locations inspected or measured on a single specimen during a process. In other words, if a relatively large percentage of a wafer may be scanned to acquire x-y data, then only a much smaller percentage of the wafer may be scanned to acquire additional z data.

One currently available system, the ABI-2000 automatic bump inspection system, available from KLA-Tencor, San Jose, Calif., may be configured to scan a wafer using bright field, white jaser imaging with image data captured using a charge coupled device ("CCD") camera and a frame-grabber. A frame-grabber is a device that may be configured to receive a signal from a detector such as a CCD camera and to convert the signal (i.e., to digitize an image). In such a system, inspection and metrology algorithms may be used to detect defects in the x-y plane and to make measurements in the x and y directions. Such a system may also be configured to re-scan, or "revisit," select locations on the wafer to acquire 3D data for individual bumps. This revisiting may use laser scanning microscopy and incremental z movement of the wafer along with additional algorithms to detect bump defects in the z plane and to make bump measurements in the z-direction.

In another example, systems developed and manufactured by Robotic Vision Systems, Inc., Canton, Mass., i.e., Model Nos. WS-1000 and WS-2000, incorporate 2D vision technology using a time delay integration ("TDI") camera and low-angle ring light or co-axial light. Such systems may be configured to first scan a wafer to detect typical 2D bump defects and surface defects. Such systems may also be configured to perform a second wafer scan using a laser triangulation technique to acquire 3D metrology measurements and to detect 3D bump defects. An example of a laser triangulation technique is illustrated in U.S. Pat. No. 6,181,472 to Liu, and is incorporated by reference as if fully set forth herein.

In yet another example, systems developed and manufactured by August Technology Corporation, Bloomington, Minn., i.e., the NSX bump inspection system, incorporate 2D vision technology using a high-resolution CCD camera and strobe illumination. Such systems may be configured to first inspect a wafer to acquire 2D data for 2D defect detection of bumps and defect detection elsewhere on the surface of the wafer. For 3D data acquisition, relatively small, select regions of the wafer may be revisited. At each of the smaller regions, the system may use automatically focusing at different vertical locations to determine the height of all bumps in the field of view.

Another example of a system for measuring 3D surface topography provides high resolution contour measurements of an object using interferometric methods. The system includes an optical head that is a moiré-type interferometer optical head employing co-sight detector phase shifting. Ronchi gratings are placed at image planes to produce moiré fringe patterns indicating the contour of the surface. The moiré images are relayed to detector planes, and CCD camera arrays view exactly the same image of the part except for the fringe pattern superimposed on the image. The images, and bucket images collected from a known reference surface needed to properly compensate the images and phase data, are used with a standard bucket phase algorithm. Output of the algorithm is analogous to the surface contour of the sample inspected. One example of such a system is illustrated in U.S. Pat. No. 6,268,923 B1 to Michniewicz et al., which is incorporated by reference as if fully set forth herein.

An additional example of a moiré-type system for 3D inspection of an object includes a source of light projected through a grid assembly. An image acquisition apparatus includes one or more cameras with an array of pixels in the form of a CCD camera. The system is used to simultaneously project at least three phase-shifted grids onto an object, to simultaneously take an image of each of the phase-shifted grids on the object to gather an intensity value for each pixel of the images, and to compute the phase for each pixel of the image using the intensity images. The above steps are performed for a reference object and the object to be measured. The difference of height between the object and the reference object for every pixel is computed by using the respective phases for each pixel, and the relief of the object for each pixel is determined using the different of height at every pixel. An example of such a system is illustrated in U.S. Patent Application Publication No. US 2002/0018118 A1 to Coulombe et al. and PCT International Publication No. WO 01/71279 A1 to Coulombe et al., which are incorporated by reference as if fully set forth herein.

There are several disadvantages to the moiré-type systems and methods for three-dimensional inspection of objects. For example, these systems and methods include complex system configurations and rely on data collected from a separate reference object. Therefore, the methods may have a lower throughput than methods that do not require a separate reference. In addition, the systems measure and use a sine wave pattern to determine the surface contour or relief of the object. Therefore, the sensitivity of the system may vary for objects of different heights. For example, the system may be more sensitive to measurements that correspond to a slope of the sine wave pattern than to measurements that correspond to a crest or valley of the sine wave pattern. In addition, using such a sine wave pattern may yield inaccurate height measurements. For example, the period of the sine wave pattern may be selected to correspond to a range of expected heights. However, if the height of an object is outside of this range, the height of the object may be inaccurately reported with an error of one or more times the range of heights.

There are several additional disadvantages to currently available systems and methods for three-dimensional inspection of bumped wafers. For example, as described above, such systems may be configured to scan a wafer more than once in series to acquire 2D and 3D data for inspection and metrology. In addition, configuration of such systems may be incompatible with rapid scanning of relatively large areas of bumped wafers. Such disadvantages will generally lower a throughput of an inspection and metrology system. Furthermore, such systems may be relatively complex due to the use of separate 2D and 3D data acquisition and processing systems. This disadvantage will generally increase cost and reduce reliability of an inspection and metrology system.

SUMMARY OF THE INVENTION

Systems and methods capable of performing high speed inspection and metrology of a specimen such as a bumped wafer are provided. An embodiment relates to a system configured to assess a dimension of a feature on a specimen. The feature may include, but is not limited to, a bump. The specimen may include, but is not limited to, a wafer. For example, the specimen may also include photonics and optoelectronic devices, thin film heads, and print heads.

The system may include an illumination system. The illumination system may include a chromatic confocal illumination system. In addition, such an illumination system may include a laser coupled to a light scanning device. Furthermore, the illumination system may include a light source configured to emit light having more than one wavelength. For example, the light source may be configured to emit broadband light. The illumination system may also include at least one optical component having substantial chromatic aberration such that the light directed to each of the multiple focal planes has different wavelengths. In this manner, the illumination system may be configured to direct light to multiple focal planes. The optical component may include an objective lens. The objective lens may also have a relatively high numerical aperture. In addition, the illumination system may be configured to scan the specimen with light at multiple focal planes substantially simultaneously. The illumination system may also be configured to scan multiple locations on the specimen with light at the multiple focal planes substantially simultaneously.

The system may also include a collection system. The collection system may be configured to collect light returned from two or more of the multiple focal planes. The collection system may include multiple collectors. Approximately all of the light returned from one of the multiple focal planes may be collected by one of the multiple collectors. For example, each of the multiple collectors may be configured to collect light from one of the multiple focal planes. The collection system may also include a single beam limiting device coupled to the multiple collectors. Alternatively, the collection system may include multiple beam limiting devices of which individual beam limiting device may be coupled to individual collectors of the multiple collectors. In a further alternative, the collection system may include a single collector configured to collect light returned from two or more of the multiple focal planes. The collected light returned from each of the multiple focal planes may include confocal imaging data. The collection system may also he configured to generate two or more signals. Each signal may be responsive to an intensity of the collected light returned from one of the two or more multiple focal planes.

In addition, the system may include a processor configured to determine a relative intensity from the generated signals. The processor may also be configured to assess a dimension of the feature. For example, a dimension of the feature on the specimen in a direction substantially perpendicular to the upper surface of the specimen may be assessed from the determined relative intensity. Such a direction may be referred to as the z-plane. In addition, such a dimension may be referred to as a 3D measurement. The assessed dimension of the feature may be used to assess if the feature is a defect such as a bump that may be too tall or too short or a bump that may have protruding vertical spikes or recessed vertical pits.

Each of the multiple focal planes may be located a different distance from an upper surface of the specimen. For example, the multiple focal planes may be located proximate upper and lower limits of a predetermined range for the dimension. The multiple focal planes may also include a focal plane located proximate the upper surface of the specimen. In this manner, a dimension of the feature in a direction substantially parallel to the upper surface of the specimen may be assessed from the collected light returned from the focal plane located proximate the upper surface of the specimen. Such a direction may be referred to as the x-y plane. In addition, such a dimension may be referred to as a 2D measurement. Therefore, confocal imaging data from multiple focal planes may be processed to make 2D and 3D measurements of features on a specimen.

Such an assessed dimension may also be used to assess if the feature is a defect such as a missing bump, an improperly located bump, a bridged bump, a large-diameter bump, or a small-diameter bump. The dimension of the feature in a direction substantially parallel to the upper surface of the specimen and the dimension of the feature in a direction substantially perpendicular to the upper surface of the specimen may be assessed substantially simultaneously. Therefore, in a single pass, such a system may be used for inspection and measurement in the x-y plane and simultaneously in the z-plane.

An additional embodiment relates to a method for assessing a dimension of a feature on a specimen. The feature may be a bump or another structure, and the specimen may include any of the specimen as described herein. The method may include directing light to multiple focal planes substantially simultaneously. Directing light to multiple focal planes may include generating light with a laser and scanning the light across the specimen. In an embodiment, the method may include scanning multiple locations on the specimen with the light at the multiple focal planes substantially simultaneously. Light directed to each of the multiple focal planes may also have a different wavelength. For example, the directed light may include broadband light. Each of the multiple focal planes may be located a different distance from an upper surface of the specimen.

The method may also include collecting light from the multiple focal planes with multiple collectors. Approximately all of the light returned from one of the multiple focal planes may be collected by one of the multiple collectors. Collecting light may include collecting light returned from two or more of the multiple focal planes with multiple collectors or with a single collector. The collected light may include confocal imaging data. In addition, the method may include generating two or more signals. Each signal may be responsive to an intensity of the collected light returned from one of the multiple focal planes. The method may further include determining a relative intensity from the generated signals. Furthermore, the method may include assessing the dimension of the feature of the specimen in a direction substantially perpendicular to the upper surface of the specimen using the relative intensity. In addition, the method may include determining if the feature is a defect using the assessed dimension of the feature.

In an embodiment, the multiple focal planes may be located proximate upper and lower limits of a predetermined range for the dimension. In an additional embodiment, the multiple focal planes may also include a focal plane located proximate the upper surface of the specimen. Therefore, the method may include assessing a dimension of the feature in a direction substantially parallel to the upper surface of the specimen using the collected light returned from the focal plane located proximate the upper surface of the specimen. The method may also include determining if the feature includes a defect using the assessed dimension of the feature in a direction substantially parallel to the upper surface of the specimen. In addition, the method may include substantially simultaneously assessing the dimension of the feature in a direction substantially parallel to the upper surface of the specimen and assessing the dimension of the feature in a direction substantially perpendicular to the upper surface of the specimen.

BRIEF DESCRIPTION OF THE DRAWINGS

Further advantages of the present invention may become apparent to those skilled in the art with the benefit of the following detailed description of the preferred embodiments and upon reference to the accompanying drawings in which.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 1:
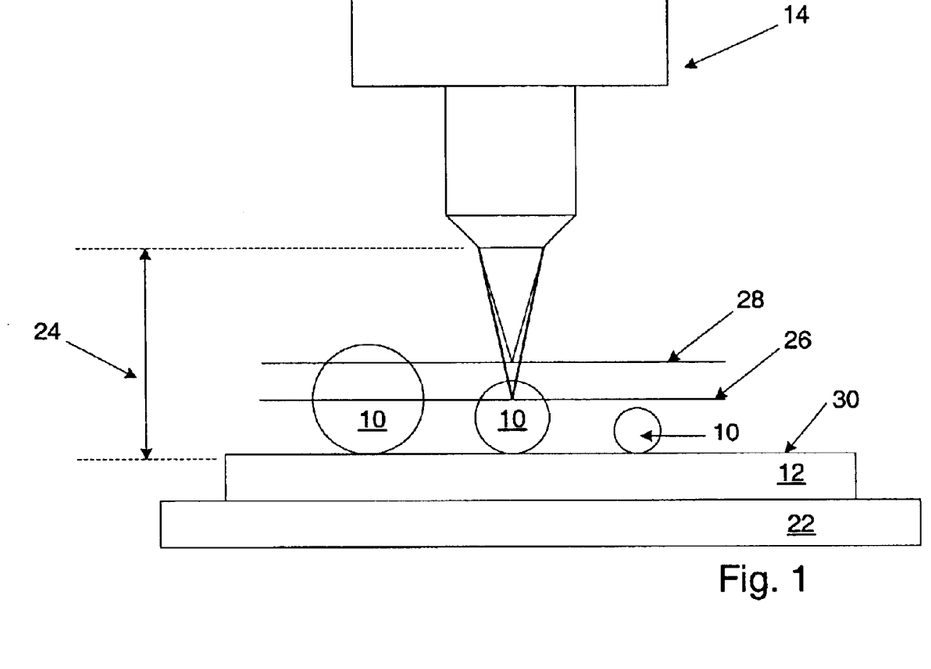
FIG. 1 depicts a partial schematic side view of an embodiment of a system configured to assess a dimension of a specimen.

FIG. 1 illustrates a partial schematic side view of a system configured to assess a dimension of feature 10 on specimen 12. Feature 10 may include, but is not limited to, a bump. As described herein, a bump may be a relatively small solder ball that may be used to couple a semiconductor device to a chip carrier. A bump, however, may also include gold bumps, solder paste bumps, or any other bumps known in the art. Specimen 12 may be a wafer. A wafer may include a monocrystalline silicon substrate suitable for the fabrication of semiconductor devices. In this manner, specimen 12 may be commonly referred to as a "bumped-wafer." The specimen may also include a wafer produced by wafer-level packaging processes such as, but not limited to, UltraCSP® available from Kulicke & Soffa Flip Chip Division, Phoenix, Ari., wCSP available from Integrated Electronics and Packaging Technologies, Inc. (Casio/Oki), Hachioji, Japan, and Super CSP™ available from Fujitsu Microelectronics America, Inc., San Jose, Calif. In addition, the specimen may include a post-saw bump or wafer-level packaging wafer on film and in film frame. Furthermore, the specimen may include individual wafer-level packages on die/package carriers.

The specimen, however, may also include a ball grid array (BGA) type package on a package carrier. The specimen may further include a thin-film head die formed on a wafer or as an individual die after saw. Furthermore, the specimen may include a micro-electro-mechanical system (MEMS) device processed on a wafer. In addition, the specimen may include, but is not limited to, photonics and optoelectronic devices such as lasers, waveguides and other passive components processed on wafers, print heads, and bio-chip devices processed on wafers. The specimen may also include any specimen known in the art that may include a feature having a dimension of interest in a plane substantially perpendicular to a plane of an upper surface of the specimen.

Figure 2:
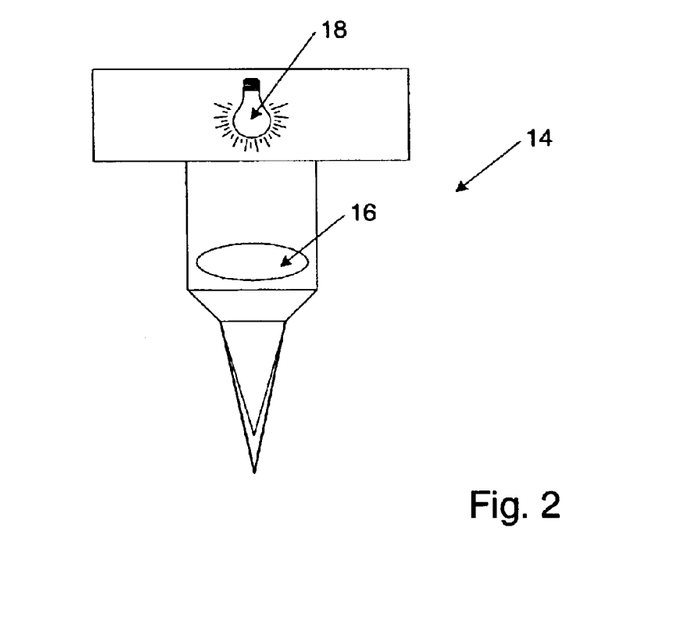
FIGS. 2 and 3 depict partial schematic side views of various embodiments of illumination systems configured to scan the specimen with light at multiple focal planes substantially simultaneously.
Figure 3:
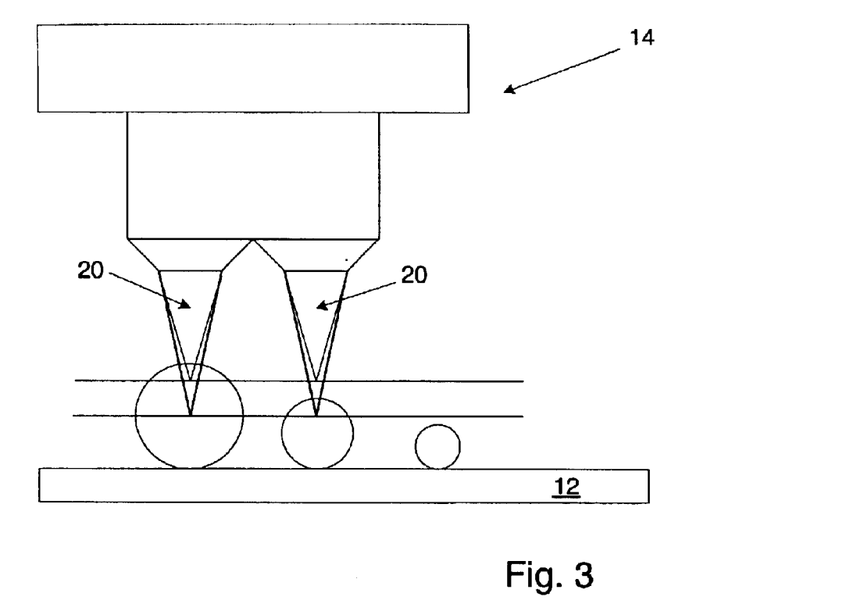

The system may include illumination system 14. The illumination system may be configured as a chromatic confocal illumination system. For example, the illumination system may be configured for bright field confocal imaging. Alternatively, the illumination system may be configured for dark field confocal imaging. An illumination system, configured for bright field or dark field confocal imaging, may include a relatively high numerical aperture ("NA") objective 16 and one or more light sources 18 configured to emit relatively short wavelength light, as shown in FIG. 2. Therefore, the illumination system may have a relatively short depth of focus. For example, a confocal illumination system may be configured to illuminate a specimen with a single point or a line. In addition, a confocal illumination system may be configured to illuminate multiple locations on a specimen with multiple points or multiple lines substantially simultaneously. For example, as shown in FIG. 3, illumination system 14 may be configured to scan multiple locations on specimen 12 with light 20 at multiple focal planes substantially simultaneously. In a dark field confocal imaging system, such imaging may be possible due to high NA diffraction limited illumination.

Such an illumination system may also include a number of additional optical components including, but not limited to, a light intensity attenuator, a spectral line bandpass filter, a polarizing beam splitter, a spatial filter, focusing optics, a collimator lens, a scan lens, a field lens, a tube lens, a quarter wave plate, a bright field cube, and folding mirrors. An example of a confocal illumination system including such additional optical components is illustrated in U.S. Pat. No. 5,912,735 to Xu and is incorporated by reference as if fully set forth herein.

Illumination system 14 may include one or more light sources 18, as shown in FIG. 2. A light source may be configured to generate a beam of light. In addition, the light source may be configured to generate a beam of light having more than one wavelength. For example, an appropriate light source may include a laser configured to emit multiple wavelengths of light. An appropriate laser may include, but is not limited to, an argon ion laser configured to emit light having wavelengths including about 455 nm, about 458 nm, about 466 nm, about 477 nm, about 488 nm, about 497 nm, about 502 nm, about 515 nm, and about 529 nm. An argon ion laser may also be configured to emit light having wavelengths in the ultraviolet and infrared ranges. Appropriate argon ion lasers are commercially available from, for example, Melles Griot, Irvine, Calif. The light source may include other light sources, however, such as a light source configured to emit broadband light. For example, the light source may be configured to a beam of broadband light that may include ultraviolet light, visible light, and/or infra-red light. A suitable broadband light source may include, but is not limited to, a mixed gas laser configured to generate light in a range of wavelengths from about 450 nm to about 647 nm. Furthermore, the system may include multiple light sources. For example, the system may include two lasers. The two lasers may be configured to generate beams of light having substantially different wavelengths.

Illumination system 14 may also include one or more filters (not shown) coupled to the light source. The filters may be configured to transmit a number of wavelengths of the light emitted by the light source. For example, the filters may be configured to transmit two or three or more wavelengths of the light. Light transmitted by the filters may be directed to a surface of a specimen 12 such that multiple wavelengths of light may be incident upon specimen 12. In addition, the illumination system may include a light scanning device (not shown) coupled to the light source. The light scanning device may be configured such that light from the light source may be directed at various angles to the upper surface of specimen 12. The light scanning device may include, for example, an acousto-optical deflector ("AOD"). An AOD may be configured to direct a beam of light at various angles. For example, deflection of a beam of light by an AOD may be controlled by a chirp generator configured to generate a chirp signal. The chirp signal may be amplified by an amplifier and may be applied to a transducer coupled to an AOD. In this manner, a sound wave may alter a property of a crystal of the AOD such that a beam of light passing through the crystal may be deflected in a manner known to those skilled in the art. For example, a chirp signal applied to a transducer may modulate a refractive index of the crystal in a periodic fashion thereby deflecting the light beam.

Alternatively, the light scanning device may include a number of deflection mirrors. For example, the system may include two deflection mirrors such as rotating polygonal mirrors, and a position of the mirrors may be altered such that light may scan across the specimen. In this manner, light from the light source may scan across specimen 12. In addition, the system may include stage 22 configured to support specimen 12. The stage may include any mechanical device configured to support a specimen known in the art. The stage may be configured to move the specimen in a first direction, and light from the light scanning device may be configured to scan the specimen in a second direction. The first and second directions may be substantially orthogonal. In this manner, an entire surface of a specimen may be scanned with light from the light source. The stage may also be configured to move in the z-direction. In this manner, height 24 between specimen 12 and illumination system 14 may be altered and/or maintained by the stage. Alternatively, illumination system 14 may be configured to move in the z-direction to alter height 24 between specimen 12 and illumination system 14. For example, height 24 may be altered prior to inspection and/or metrology of a specimen and may be maintained substantially constant throughout an inspection and/or metrology process.

Illumination system 14 may be configured to direct light to multiple focal planes. As such, the illumination system may scan the specimen with light at multiple focal planes substantially simultaneously. For example, illumination system 14 may include at least one optical component such as objective lens 16, as shown in FIG. 2, having substantial chromatic aberration. At least the one optical component may include, for example, a microscope objective that may not be substantially color-corrected such that chromatic aberration of the light incident upon specimen 12 may be realized. When light of different wavelengths is passed through optics with sufficient chromatic aberration, the focal planes of different wavelengths of light may be at different distances from the upper surface of the specimen. In this manner, light emitted from the light source having different wavelengths may be directed to different focal planes at various vertical locations.

As shown in FIG. 1, therefore, illumination system 14 may be configured to direct light to focal plane 26 and focal plane 28. Focal plane 26 and focal plane 28 may include light of different wavelengths. Each of the focal planes may be located a different distance from upper surface 30 of specimen 12. For example, focal plane 26 may be located closer to an upper surface of specimen 12 than focal plane 28. If the light incident upon specimen 12 includes multiple wavelength, then, in a confocal system, such light may establish multiple planes of peak focus for each wavelength at different heights relative to the surface of the specimen. For example, if the light incident upon specimen 12 includes blue and green wavelengths, then a plane of peak focus for blue wavelength light m ay be located farther away from the upper surface of the specimen than a plane of peak focus of green wavelength light. Illumination system 14, however, may also be configured to direct light to more than two focal planes.

The system may also include a collection system. FIGS. 4a–4e illustrate partial schematic views of various embodiments of a collection system. The collection system may be configured to collect light returned from two or more of the multiple focal planes. The collection system may be further configured to generate two or more signals. Each signal may be responsive to an intensity of the collected light returned from one of the two or more multiple focal planes. For example, the collection system may include multiple collectors 32, as shown in FIGS. 4a–4d. Although two and three collectors are shown in these Figures, any number of collectors may be used depending upon, for example, the number of focal planes used to scan the specimen. The number and the arrangement of the collectors may also vary depending upon, for example, physical and mechanical restraints of the system.

The collection systems shown in FIGS. 4a–4d may also include one or more dichroic beamsplitters 34. A dichroic beamsplitter may be used to transmit light depending upon its wavelength rather than on its plane of vibration. For example, the dichroic beamsplitter may transmit one color while reflecting a second color when illuminated with multiwavelength light. The dichroic beamsplitter may include, for example, cemented right angle prisms coated with a wavelength specific anti-reflective coating or any other optical component configured to separate light based upon wavelength known in the art. In this manner, approximately all of the light returned-from one of the multiple focal planes may be collected by one of the multiple collectors. As used herein, "approximately all of the light returned from one of the multiple focal planes" refers to substantially all of the light returned from the specimen minus negligible amounts of light lost due to, for example, light scattering and/or marginalities of the optical components of the collection system. For example, approximately all of the light returned from one of the multiple focal planes does not refer to light from a focal plane intentionally split into multiple channels, each containing a portion of the light suitable for collection, which are directed to a plurality of collectors. For example, beamsplitter 34 may be configured to reflect blue light and to transmit green light. In this manner, one of the collectors may collect blue light while the other collector collects green light. As such, each of the multiple collectors may be configured to collect light returned from one of the multiple focal planes.

Figure 4A:
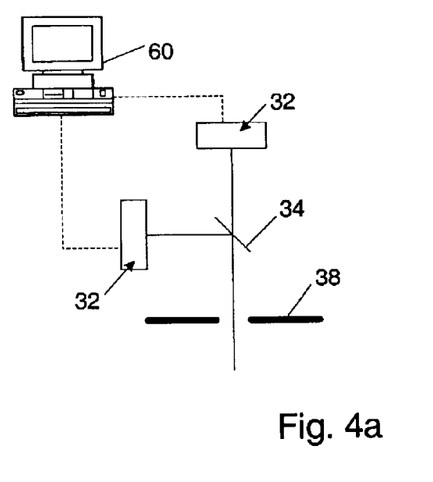
FIGS. 4a–4e depict partial schematic views of various embodiments of collection systems that include one or more collectors.
Figure 4B:
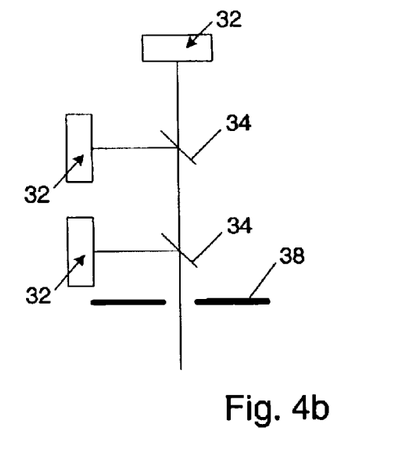
Figure 4C:
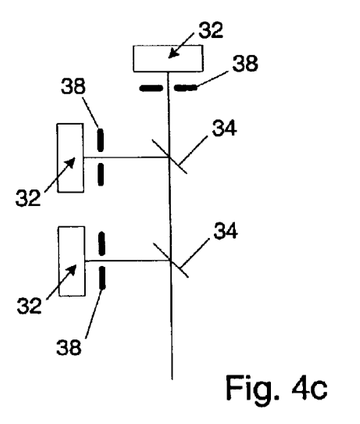
Figure 4D:
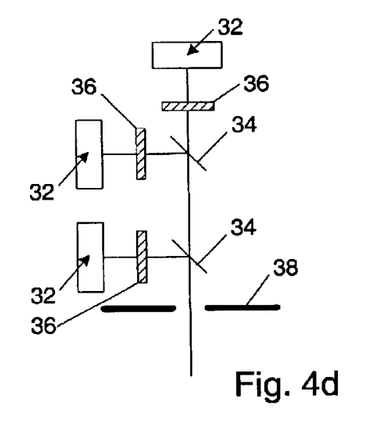
Figure 4E:
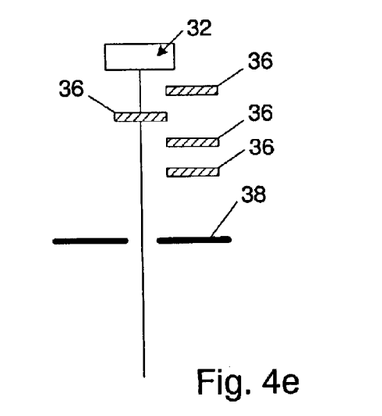

Alternatively, the collection system may include a single collector as shown in FIG. 4e. The system may be configured such that the single collector may be time-shared by light returned from the surface of the specimen. In an example, a plurality of spectral filters 36 may be coupled to the single collector. A first spectral filter may be placed in front of the single collector such that light from only one of the multiple focal planes may be collected. After collection of light from this focal plane, a second spectral filter may be placed in front of the single collector such that light from a different focal plane may be collected. In this manner, collection of light from each of the multiple focal planes may be performed sequentially. In addition, any other method of time-sharing a single collector known in the art may also be used to collect light from at least two or more of the multiple focal planes. In a similar manner, collectors of a system that includes multiple collectors may also be coupled to one or more spectral filters 36, as shown in FIG. 4d. In this manner, each of the collectors may also be time-shared. The spectral filter place in front of the collectors may vary depending upon a specimen being measured and/or inspected. Such a system may provide greater flexibility for metrology and/or inspection of specimen that vary greatly in dimension, material, and/or feature types formed thereon.

The single collector may include any light sensitive device including imaging and non-imaging devices known in the art such as a photomultiplier tube ("PMT"), avalanche photodiodes, a charge coupled device ("CCD") camera, a time delay integration ("TDI") camera, a video camera, a split photodiode detector, a conventional spectrophotometer, a quad-cell detector, a linear sensor array, and a position sensitive detector. The multiple collectors may include any combination of such light sensitive devices. The collection system may include a number of additional optical components such as any optical component known-in the art.

In either brightfield or darkfield confocal imaging, the collection system may include beam limiting device 38, as shown in FIG. 4e, coupled to collector 32. A beam limiting device may include, for example, an aperture. In this manner, an illuminated spot on the specimen may be imaged through an aperture coupled to a collector. Such an aperture and collector may include a pinhole and a single point detector, in the case of single point illumination. In this manner, the collector may be effectively a pinhole. A lateral dimension of the pinhole may vary depending on, for example, a lateral dimension of the illuminated point on the specimen and a magnification that may exist between the sample plane and the pinhole plane. Alternatively, the beam limiting device may include a slit, which may be coupled to a linear detector array, in the case of line illumination. As shown in FIGS. 4a, 4b, and 4d, a single beam limiting device 38 may be coupled to multiple collectors 32. Alternatively, as shown in FIG. 4c, the collection system may include multiple beam limiting devices 38 of which individual beam limiting devices are coupled to individual collectors 32.

In dark field confocal imaging, the illuminated spot on the specimen may be imaged using an NA that may be less than the illumination NA, through a beam limiting device in front of a collector. The specimen and illumination spot, beam limiting device, or a combination thereof may be scanned to collect information about an area on the specimen. In this manner, the collected light returned from each of the multiple focal planes may include confocal imaging data.

Figure 5:
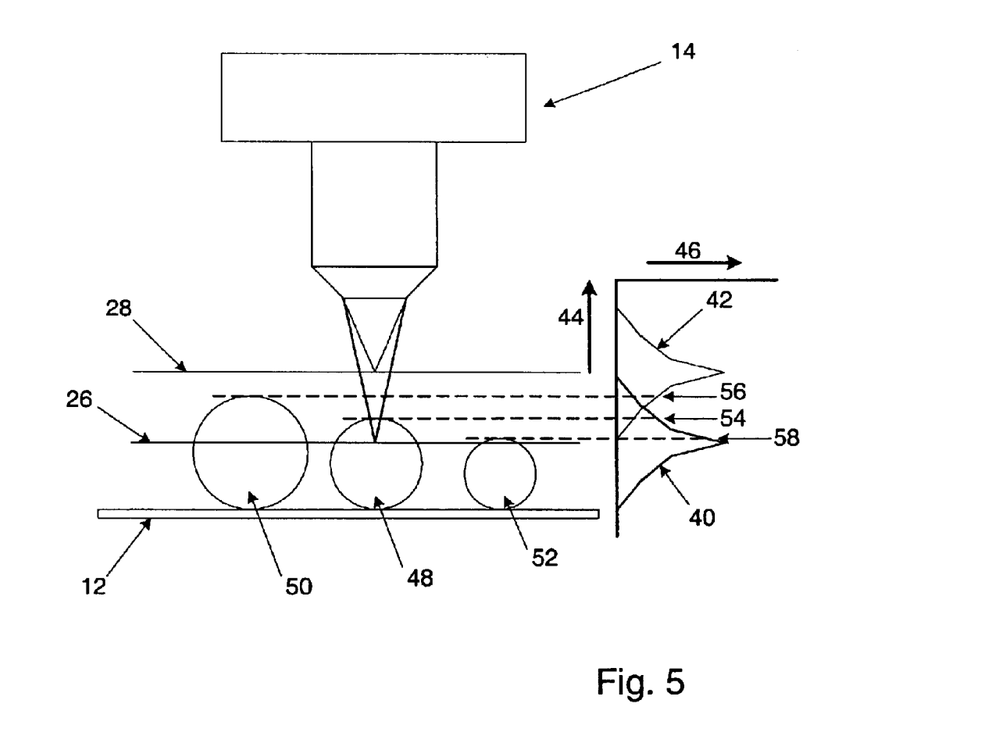
FIG. 5 depicts a partial schematic side view of an embodiment of a system configured to assess a dimension of a feature of a specimen.

By separate collection of light returned from multiple focal planes, either through use of multiple collectors or by time-sharing a single collector, the relative intensity of light returned from various focal planes may be compared. For example, when the multiple focal planes of light scan across a feature on the specimen, the intensity of the light from each of the focal planes may generally differ. For example, as shown in FIG. 5, light returned from focal plane 26 may have a range of intensities that may include intensities in spectrum 40. Light returned from focal plane 28 may have a range of intensities that may include intensities in spectrum 42. Spectrum 40 may be laterally offset from spectrum 42 along axis 44. Therefore, the system may have a unique intensity ratio. As shown in FIG. 5, the wavelengths of light incident upon the specimen may be selected such that the intensity response curves cross in low points. A light sensitive portion of a collector may generate an analog signal in response to detected light from each of the focal planes. The generated signals may digitized by an analog/digital converter (not shown) coupled to the collector, and the digital data may be sent through an interface to processor 60, as shown in FIG. 4a. Each of the embodiments illustrates in FIGS. 4b–4e may be similarly configured. The processor may be configured to determine a relative intensity of light from one focal plane to light from another focal plane from the generated signals.

The processor may also be configured to assess the dimension of the feature on the specimen in a direction substantially perpendicular to an upper surface of the specimen using the relative intensity. For example, comparison of the relative intensity may yield height or depth information. For example, an intensity of light returned from each focal plane may vary along axis 44, which may correspond to a height of feature in the focal plane. Axis 46 may correspond to a value of the intensity. As shown in FIG. 5, bumps 48, 50, and 52 have different heights and light returned from each bump has a different relative intensity 54, 56, and 58, respectively. Therefore, a relative intensity may be used to determine a dimension of the feature on the specimen. For example, a dimension of the feature on the specimen in a direction substantially perpendicular to the upper surface of the specimen such as a height of the feature may be assessed from the relative intensity. For the data to be substantially valid and substantially accurate, the features being scanned with the light should have approximately consistent optical properties for the wavelengths of the incident light. In addition, if the system is configured to have a unique intensity ratio as described above, then two substantially different heights may not yield indistinguishable relative data. The 3D height information may be quantitative over a range where accurate measurement of the relative intensity may be made. Outside of this ratio range, data in the z-dimension may be reported as greater than a first value "x" on one side and less than a second value "y" on the other side.

The assessed dimension of the feature may be used to assess if the feature comprises a defect such as a 3D defect. For example, the processor may be configured to compare the assessed dimension to a predetermined range for the dimension. A predetermined range may vary depending on, for example, a target value for the dimension and a range of acceptable values for the dimension on either side of the target value. In this manner, a feature may be determined to be a defect if the assessed dimension is outside of this range.

In an embodiment, the multiple focal planes may be located proximate upper and lower limits of a predetermined range for the dimension. For example, the illumination system may be configured such that multiple focal planes may be located approximately above and below upper and lower limits, respectively, of a predetermined range for a dimension of a feature. For example, focal plane 26 may be located approximately below a lower limit of the predetermined range. Focal plane 28 may be located approximately above an upper limit of the predetermined range. In this manner, the system may be configured such that a height of a feature within at least the predetermined range may be assessed by the system. As such, a relative intensity that may be outside of the range where accurate measurement may be made, as described above, may indicate that a feature is a defect.

As shown in FIG. 5, for example, bump 48 may be a feature on the specimen having a dimension in a plane substantially perpendicular to the upper surface of the specimen within the predetermined range. Bump 52, however, may be a 3D defect such as a bump that is too short or that may have a recessed vertical pit. In addition, bump 50 may be a 3D defect such as a bump that is too tall or a bump that may have a protruding vertical spike. Therefore, the system may be configured to assess a dimension of features having either acceptable or unacceptable dimensions. For example, the relative intensity of the light returned from multiple focal planes may indicate that bumps 50 and 52 are 3D defects. In addition, the relative intensity of light returned from multiple focal planes 26 and 28 may indicate the type of 3D defects that bumps 50 and 52 may be.

The processor may also include an image processing device coupled to the system. An image processing device may be a parallel processing system that may be commonly used by the machine vision industry. The image processing device may be configured to generate an image of an illuminated area of specimen 12. The image processing device may also be coupled to a host computer that may be configured to control the system and to perform data processing functions. For example, data processing functions may include determining a presence of defects on a surface of a specimen by comparing output signals of light sensitive devices generated by illuminating two different locations on the specimen.

In addition, the illumination-system may be configured such that one of the multiple focal planes may be located proximate the upper surface of specimen 12. For example, a focal plane closest to the upper surface of the specimen may be positioned to have sufficient intensity at the upper surface of the specimen. In this manner, a dimension of feature 10 in a direction substantially parallel to the upper surface of the specimen such as a width, length, or diameter may be assessed from the collected light returned from the focal plane located proximate the upper surface of the specimen. Such a dimension may be used to assess if the feature is a defect such as a 2D dimensional defect as described herein. For example, bridging defects and satellite defects as well as etch residue may be detected by scanning with the laser wavelength that may have a maximum intensity proximate the specimen surface. In this manner, the system may be used to acquire data for full-surface inspection. Therefore, 2D defects may be detected without using white light imaging and a CCD camera collection system. In an additional embodiment, a third focal plane may be positioned near the upper surface of the specimen while two focal planes bracket a height range of interest for better resolution in the z-direction.

As described herein, a single laser scanning system with multiple wavelengths and engineered chromatic aberration may provide both 2D and 3D inspection and/or metrology. In this manner, independent techniques and hardware may not be required to perform both 2D and 3D inspection and/or metrology. In addition, a dimension of a feature such as a width and a dimension of the feature in a direction substantially perpendicular to the upper surface of the specimen may be assessed substantially simultaneously. In this manner, the system may be configured to acquire and process 2D and 3D data in a single pass. Such a system, therefore, may have a significantly higher throughput than currently available systems. In addition, such a system may be configured to acquire and process 3D data only. Such a system may also have a significantly higher throughput than systems that may be configured to perform only 3D metrology and/or inspection.

Figure 6:
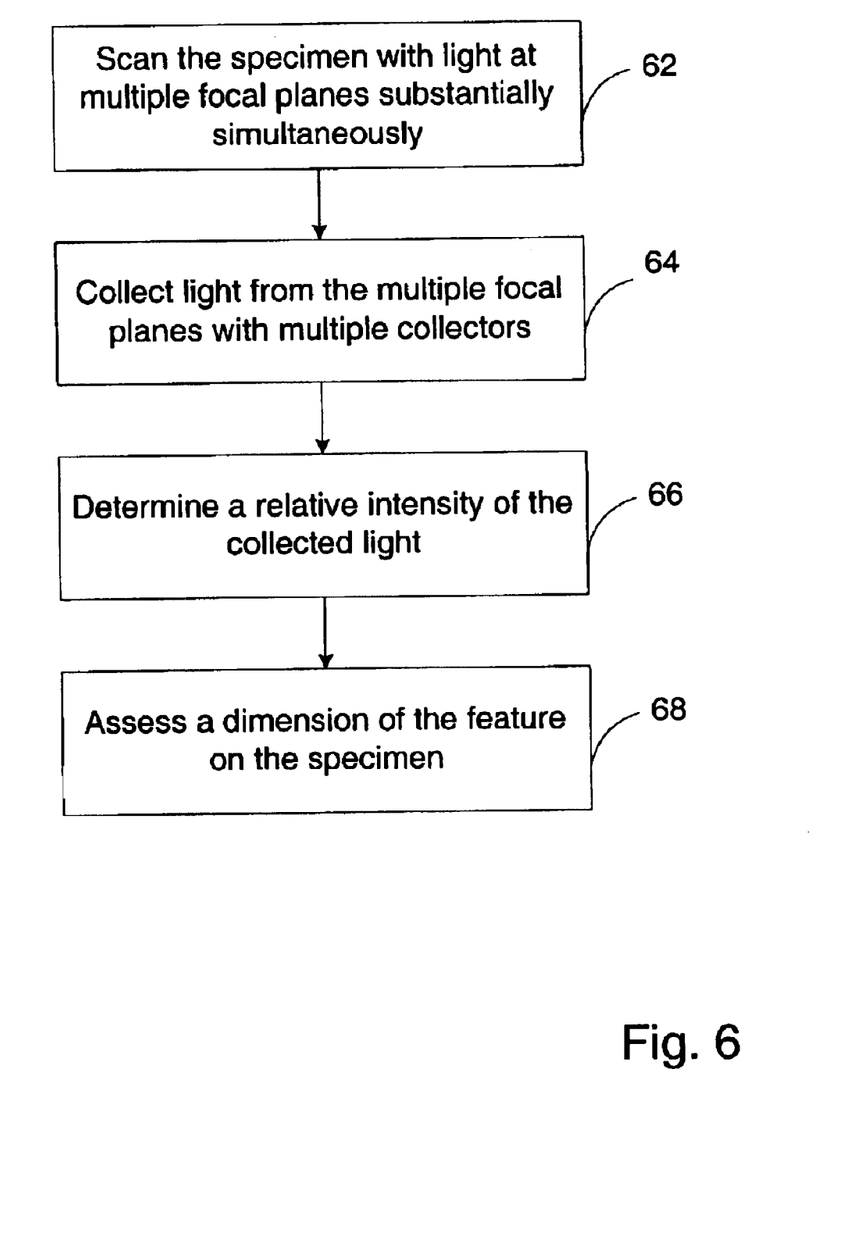
FIG. 6 depicts a flow chart illustrating a method for assessing a dimension of a feature of a specimen.

FIG. 6 illustrates a flow chart of an embodiment of a method for assessing a dimension of a feature on a specimen. The feature may be a bump or another structure as described herein, and the specimen may include any of the specimen as described herein. As shown in step 62, the method may include scanning the specimen with light at multiple focal planes substantially simultaneously. For example, scanning the specimen may include directing light to multiple focal planes. Directing light to multiple focal planes may include generating light with a laser and scanning the generated light across the specimen. The method may also include scanning multiple locations on the specimen with light at multiple focal planes substantially simultaneously. Light directed to each of the multiple focal planes may also have a different wavelength. For example, the directed light may include broadband light. Each of the multiple focal planes may be located a different distance from an upper surface of the specimen. In an embodiment, the multiple focal planes may be located proximate upper and lower limits of a predetermined range for the dimension, as described above.

The method may also include collecting light returned from two or more of the multiple focal planes with multiple collectors, as shown in step 64. Approximately all of the light returned from one of the multiple focal planes may be collected by one of the multiple collectors, as described above. Alternatively, collecting light may include collecting light returned from two or more of the multiple focal planes with a single collector. The collected light may include confocal imaging data. In addition, the method may include generating two or more signals. Each signal may be responsive to an intensity of the collected light returned from one of the multiple focal planes. The method may further include determining a relative intensity of the collected light, for example, using the generated signals, as shown in step 66. Furthermore, the method may include assessing the dimension of the feature of the specimen in a direction substantially perpendicular to the upper surface of the specimen using the determined relative intensity, as shown in step 68. In addition, the method may include determining if the feature is a defect using the assessed dimension of the feature.

The multiple focal planes may include a focal plane located proximate the upper surface of the specimen. Therefore, the method may include assessing a dimension of the feature in a direction substantially parallel to the upper surface of the specimen using the collected light returned from the focal plane located proximate the upper surface of the specimen. The method may also include determining if the feature is a defect using the assessed dimension of the feature in a direction substantially parallel to the upper surface of the specimen. In addition, the method may include substantially simultaneously assessing the dimension of the feature in a direction substantially parallel to the upper surface of the specimen and assessing the dimension of the feature in a direction substantially perpendicular to the upper surface of the specimen.

Further modifications and alternative embodiments of various aspects of the invention may be apparent to those skilled in the art in view of this description. For example, systems and methods for three-dimensional inspection and/or metrology of a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to assess a dimension of a feature on a specimen, comprising:

an illumination system configured to scan the specimen with light at multiple focal planes substantially simultaneously;

a collection system comprising multiple collectors, wherein approximately all light returned from one of the multiple focal planes is collected by one of the multiple collectors; and a processor configured to determine a relative intensity of the collected light from one of the multiple focal planes to the collected light from another of the multile focal planes, wherein the processor is further configured and to assess the dimension of the feature on the specimen in a direction substantially perpendicular to an upper surface of the specimen using the relative intensity value.

2. The system of claim 1, wherein the collection system further comprises a single beam limiting device coupled to the multiple collectors.

3. The system of claim 1, wherein the collection system further comprises multiple beam limiting devices of which individual beam limiting devices are coupled to individual collectors of the multiple collectors.

4. The system of claim 1, wherein the multiple focal planes are located different distances from the upper surface of the specimen.

5. The system of claim 1, wherein the multiple focal planes are located proximate upper and lower limits of a predetermined range for the dimension.

6. The system of claim 1, wherein the multiple focal planes comprise a focal plane located proximate the upper surface of the specimen, and wherein a dimension of the feature in a direction substantially parallel to the upper surface of the specimen can be assessed from the collected light returned from the focal plane located proximate the upper surface of the specimen.

7. The system of claim 6, wherein the dimension of the feature in the direction substantially parallel to the upper surface of the specimen can be used to assess if the feature comprises a defect.

8. The system of claim 1, wherein the illumination system is further configured to scan multiple locations on the specimen with the light at the multiple focal planes substantially simultaneously.

9. The system of claim 1, wherein the illumination system comprises a chromatic confocal illumination system.

10. The system of claim 1, wherein the collected light comprises confocal imaging data.

11. The system of claim 1, wherein the illumination system comprises an objective lens having a relatively high numerical aperture and substantial chromatic aberration such that the light at the multiple focal planes comprises different wavelengths.

12. The system of claim 1, wherein the dimension of the feature can be used to assess if the feature comprises a defect.

13. The system of claim 1, wherein the feature comprises a bump, and wherein the specimen comprises a wafer.

14. A method for assessing a dimension of a feature on a specimen, comprising:

scanning the specimen with light at multiple focal planes substantially simultaneously;

collecting light from the multiple focal planes with multiple collectors wherein approximately all light returned from one of the multiple focal planes is collected by one of the multiple collectors;

determining a relative intensity value of the collected light from one of the multiple focal planes to the collected light from another of the multiple focal planes; and assessing the dimension of the feature of the specimen in a direction substantially perpendicular to an upper surface of the specimen using the relative intensity value.

15. The method of claim 14, wherein the multiple focal planes are located proximate upper and lower limits of a predetermined range for the dimension.

16. The method of claim 14, wherein the multiple focal planes is a focal plane located proximate the upper surface of the specimen, the method further comprising assessing a dimension of the feature in at direction substantially parallel to the upper surface of the specimen using the collected light returned from the focal plane located proximate the upper surface of the specimen.

17. The method of claim 16, further comprising determining if the feature comprises a defect using, the dimension of the feature in the direction substantially parallel to the upper surface of the specimen.

18. The method of claim 14, wherein said scanning comprises scanning multiple locations on the specimen with the light at the multiple focal planes substantially simultaneously.

19. The method of claim 14, further comprising determining if the feature comprises a defect using the assessed dimension of the feature.

20. The method of claim 14, wherein the feature comprises a bump, and wherein the specimen comprises a wafer.

* * * * *